United States Patent
Vedage et al.

[11] Patent Number: 6,121,493
[45] Date of Patent: Sep. 19, 2000

[54] ISOMERIZATION OF CYCLOHEXYLAMINES TO PRODUCE THEIR THERMODYNAMIC ISOMERIC FORM

[75] Inventors: Gamini Ananda Vedage, Bethlehem; John Nelson Armor, Orefield, both of Pa.

[73] Assignee: Air Products and Chemicals, Inc., Allentown, Pa.

[21] Appl. No.: 08/040,311

[22] Filed: Mar. 30, 1993

[51] Int. Cl.$^7$ .................................................. C07C 209/00
[52] U.S. Cl. .................................................. 564/444
[58] Field of Search ................... 564/444, 450, 564/451

[56] References Cited

U.S. PATENT DOCUMENTS

| | | | |
|---|---|---|---|
| 2,511,028 | 6/1950 | Whitman | 564/451 |
| 2,606,924 | 8/1952 | Whitman | 564/451 |
| 2,606,925 | 8/1952 | Whitman | 564/450 |
| 2,606,928 | 8/1952 | Barkdoll et al. | 564/451 |
| 3,155,724 | 11/1964 | Arthur | 564/444 |
| 3,347,917 | 10/1967 | Arthur | 564/451 |
| 3,445,516 | 5/1969 | Cross | 564/451 |
| 3,520,928 | 7/1970 | Greco | 564/450 |
| 3,558,703 | 1/1971 | Adam et al. | 564/451 |
| 3,591,635 | 7/1971 | Farrissey et al. | 564/451 |
| 3,634,512 | 1/1972 | Peebeu et al. | 564/451 |
| 3,679,746 | 7/1972 | Brake | 564/444 |
| 3,711,550 | 1/1973 | Brake | 564/444 |
| 3,766,272 | 10/1973 | Brake | 564/444 |
| 3,829,490 | 8/1974 | Mueller et al. | 564/444 |
| 4,020,104 | 4/1977 | Richter | 564/444 |
| 4,503,249 | 3/1985 | Nowack et al. | 564/385 |
| 4,946,998 | 8/1990 | Casey | 564/451 |

FOREIGN PATENT DOCUMENTS

| | | |
|---|---|---|
| 46-016981 | 5/1971 | Japan . |
| 46-030835 | 9/1971 | Japan . |
| 1122609 | 8/1968 | United Kingdom . |

OTHER PUBLICATIONS

Kirk–Othmer Encyclopedia of Chemical Technology, 3d ed., 1979, v.5. month unavailable.
Kirk–Othmer Encyclopedia of Technology, 3d ed., vol. 5, pp. 39–40 (1979).

Primary Examiner—Samuel Barts
Attorney, Agent, or Firm—Mary E. Bongiorno

[57] ABSTRACT

This invention relates to an isomerization process wherein hydrogenated aromatic amines are substantially isomerized to their thermodynamic form. These hydrogenated aromatic amines are presented by the formulas:

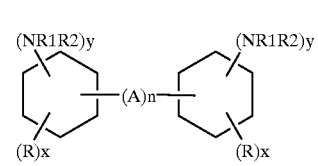

I

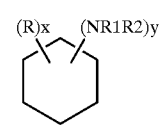

II wherein R is hydrogen or $C_{1-6}$ aliphatic, R1 and R2 are hydrogen or $C_{1-6}$ aliphatic, A is $C_{1-4}$ or NH; n is 0–2, x is 1–3 and y is 1 to 2 except the sum of the y groups in Formula I may be 1.

The improvement in the process comprises using a catalytic system comprising cobalt preferably in combination with another Group VIII metal selected from rhodium, ruthenium, platinum, and palladium and the metal, copper. Preferably the catalyst comprises cobalt in combination with rhodium or ruthenium wherein the weight ratio of cobalt to rhodium or ruthenium, calculated on metal content, is from about 0.2 to 100 weight parts cobalt per weight part rhodium or ruthenium and the isomerization is carried out in the presence of hydrogen.

11 Claims, No Drawings

ISOMERIZATION OF CYCLOHEXYLAMINES TO PRODUCE THEIR THERMODYNAMIC ISOMERIC FORM

FIELD OF THE INVENTION

This invention pertains to a process for isomerizing hydrogenated aromatic amines to produce a thermodynamic isomer mixture.

BACKGROUND OF THE INVENTION

There is substantial literature in the art with respect to the hydrogenation of aromatic amines, including bridged aromatic amines, e.g., methylenedianiline to produce 4,4'-methylenedi(cyclohexylamine), also called bis(para-aminocyclohexyl)methane, bis(4-aminocyclohexyl)methane and PACM.

The hydrogenated form of these aromatic amines, typically exists as a mixture of isomers, e.g., the cis,cis- (c,c); cis,trans- (c,t); and trans,trans- (t,t). Often it is desirable to produce a product having a specific isomer content as the isomer content in the mixture not only influences the physical form of the mixture but also influences the properties of products in which they are incorporated. In the case of PACM, a low trans,trans- isomer content (20%) in the mixture, commonly referred to as PACM-20, exists as a liquid product while a mixture high in trans,trans- isomer content (48%), commonly referred to as PACM-48, leads to a solid form. For certain applications, such as the manufacture of polyamide fibers and epoxy additives, it often is beneficial to use PACM-48 instead of PACM-20.

Commercially, PACM-48 is produced through continuous processing conditions, where catalyst loading and reactor residence times are sufficient to yield the product of thermodynamic control. Batch processing conditions produce PACM-48 from MDA inefficiently due to excessive reaction times required for complete isomerization to the product of thermodynamic control.

Some of the early hydrogenation work to produce aromatic amines, such as, PACM, was done by Whitman and Barkdoll, et al. and their work is set forth in a series of U.S. Patents, e.g., U.S. Pat. Nos. 2,511,028; 2,606,924; 2,606,925; and 2,606,928. Basically the processes described in these patents involve the hydrogenation of methylenedianiline at pressures in excess of 200 psig, preferably in excess of 1,000 psig, at temperatures organic solvent is used in the hydrogenation process. Typically, a liquid product having a trans,trans- content of 15–23% is obtained. Examples of ruthenium catalysts utilized for the hydrogenation process include ruthenium oxides such as ruthenium sesquioxide and ruthenium dioxide; and ruthenium salts.

U.S. Pat. Nos. 3,347,917; 3,711,550; 3,679,746; 3,155,724; 3,766,272 and British Patent 1,122,609 disclose various isomerization processes and hydrogenation processes to produce PACM containing high trans,trans- isomer content; i.e. an isomer content near equilibrium typically 50% trans,trans, 43% cis,trans- and 7% cis,cis-. As in the early work ruthenium catalysts usually were used to effect isomerization. Higher temperatures and longer reaction times were required to produce the high trans,trans- product and, in addition, considerable deamination of product took place.

A wide variety of catalytic systems have been developed for the hydrogenation and isomerization of aromatic amine, and typical catalytic systems are represented in the following patents:

U.S. Pat. No. 3,591,635 discloses the use of rhodium on alumina as a catalyst for the hydrogenation of methylenedianiline.

U.S. Pat. No. 4,946,998 discloses processes for the hydrogenation of methylenedianiline contaminated with impurities utilizing a mixture of rhodium and ruthenium as the catalyst. A hydrogenated methylene-dianiline product having a trans,trans- isomer content of from about 14 to 28% is prepared using the mixed metal catalyst system, although higher trans,trans- content can be achieved through high temperature, long reaction times, and high ruthenium concentration. The presence of rhodium permits lower operating temperatures and reduces the percent trans,trans- isomer.

U.S. Pat. No. 3,520,928 discloses the low pressure hydrogenation of mineral acid salts of aromatic primary amines and aqueous solution using a platinum or palladium catalyst.

U.S. Pat. No. 3,558,703 and U.S. Pat. No. 3,634,512 disclose the catalytic hydrogenation of diaminodiphenyl alkanes and ethers utilizing a cobalt or nickel catalyst promoted with manganese and base modified derivatives thereof ('512). The '703 patent discloses that other conventional catalysts may be incorporated into the catalyst component of cobalt or nickel, and such metals include copper, chromium, nickel, tungsten, molybdenum, platinum, palladium and ruthenium in amounts up to about 10% by weight.

U.S. Pat. No. 3,445,516 discloses the hydrogenation of toluenediamine utilizing a variety of catalysts including Raney nickel, Raney cobalt, cobalt oxide and mixtures of cobalt oxide and alkaline earth metal oxide, such as calcium oxide in combination with sodium carbonate.

U.S. Pat. Nos. 3,679,746 and 4,020,104 disclose the isomerization of a PACM and PACM-type product low in trans,trans-isomer content to one of high trans,trans- isomer content using ammonia and a ruthenium catalyst.

SUMMARY OF THE INVENTION

This invention relates to an improved process for isomerizing hydrogenated aromatic amines such as 4,4'-methylenedi(cyclohexylamine) (PACM) by the catalytic isomerization of the hydrogenated aromatic amines to produce a reaction product which is substantially in thermodynamic equilibrium. The improvement in the process comprises using a catalytic system comprising cobalt preferably in combination with another Group VIII metal selected from rhodium, ruthenium, platinum, and palladium and the metal, copper. Preferably the catalyst comprises cobalt in combination with rhodium or ruthenium wherein the weight ratio of cobalt to rhodium or ruthenium, calculated on metal content, is from about 0.2 to 100 weight parts cobalt per weight part rhodium or ruthenium and the isomerization is carried out in the presence of hydrogen.

There are several advantages associated with this process. These include:

an ability to effect isomerization of hydrogenated aromatic amines at relatively low hydrogen pressures, e.g., 100 psig and lower at acceptable reaction rates;

an ability to isomerize hydrogenated methylene bridged dianilines to a product having an isomer distribution approximating that of the thermodynamic form;

an ability to isomerize hydrogenated bridged aromatic amines without effecting significant deamination of the feed or product; and, an ability to use the catalyst for continued periods of time with only modest maintenance or regeneration techniques.

DETAILED DESCRIPTION OF THE INVENTION

This invention relates to an improvement in the conventional isomerization of hydrogenated aromatic amines or cyclohexylamines and these amines are represented by the formulas:

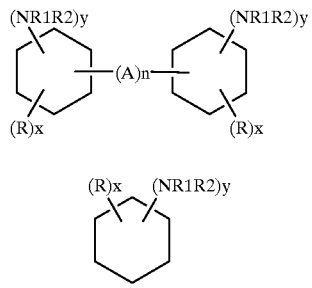

I

II wherein R is hydrogen or $C_{1-6}$ aliphatic, R1 and R2 are hydrogen, or $C_{1-6}$ aliphatic, A is $C_{1-4}$ alkyl, or NH, n is 0 or 1, x is 1–3 and y is 1–2 except the sum of the y groups in Formula I may be 1. By the practice of this invention, one is able to selectively produce an isomerized reaction product in high selectivity to the thermodynamic isomer form with excellent reaction rates. The hydrogenated aromatic amines or cyclohexylamines useful in the practice of the process are hydrogenated bridged polynuclear aromatic amines or mononuclear aromatic amines, i.e., cyclohexylamines. These can be substituted with various substituents such as aliphatic groups containing from 1–6 carbon atoms. Further, the amine group can be substituted with aliphatic groups such as alkyl or alkanol groups resulting in secondary and tertiary amine substituents. Examples of bridged cyclohexylamines which can be isomerized include bis(para-aminocyclohexyl)methane; bis(para-amino-2-methylcyclohexyl)methane; bis(diaminocyclohexyl)methane; bis(diaminocyclohexyl)propane; bicyclohexylamine; bi(3-methylclohexylamine); N-$C_{1-4}$-aliphatic derivatives and N,N'$C_{1-4}$ aliphatic secondary and tertiary amine derivatives of the above bridged cyclohexylamines. Examples of mononuclear cyclohexylamines include 2,4- and 2,6-cyclohexanediamine, alkylated derivatives of cyclohexanediamine, such as, 1-methyl-3,5-diethyl-2,4 or 2,6-diaminocyclohexane, commonly known as diethylcyclohexanediamine; diisopropylcyclohexanediamine, mono-isopropyl cyclohexanediamine, tert-butyl-2,4- and 2,6-cyclohexanediamine, cyclopent-cyclohexanediamine; cyclohexanediamine, cyclohexaneamine, alkylated derivatives of cyclohexaneamine, e.g., ortho-methylcyclohexylamine, dimethylcyclohexanediamine, and the N and N,N'$C_{1-4}$ aliphatic secondary and tertiary amine derivatives of the mononuclear cyclohexanemonoamines and mononuclear cyclohexanediamines.

The isomerization process is carried out under liquid phase conditions, such liquid phase conditions being maintained typically by carrying out the isomerization in the presence of a solvent. Although as reported in the art, it is possible to produce the reaction product in the absence of a solvent, the processing usually is much simpler when a solvent is employed. Representative solvents suited for practicing the invention include saturated aliphatic and alicyclic hydrocarbons such as cyclohexane, hexane, and cyclooctane; low molecular weight alcohols, such as methanol, ethanol, isopropanol; and aliphatic and alicyclic hydrocarbon ethers, such as n-propyl ether, isopropyl ether, n-butyl ether, amyl ether, tetrahydrofuran, dioxane, and dicyclohexylether. Tetrahydrofuran is preferred. Although in some processes water can be used as a cosolvent, it is preferred that the system be maintained in an anhydrous state or at least maintained such that the water concentration is less than 0.5% by weight. Water, when present in the system, tends to increase the amount of by-product alcohols and heavy condensation products and it tends to deactivate the catalyst system.

When a solvent is used, concentrations as low as 50% by weight based upon the cyclohexylamine introduced into the reaction zone are common and typically the solvent is used at levels from about 75 to about 200% by weight of the starting compound. Under some circumstances solvent amounts as high as 1000 to 2000% based upon the weight of cyclohexylamine are used. The downside to high solvent use is cost and recovery burdens.

The isomerization is carried out principally in a batch process although it is possible to operate the plant continuously. Temperatures usually used for the isomerization process range from about 130 to 220° C. with preferred temperatures of from about 170 to 195° C. The thermodynamic form of isomeric product can be readily obtained at hydrogen pressures as low as from about 100 to 1000 psig, thus providing for lower equipment costs and operating costs. When the pressure is raised toward the upper end of the operating range and above, higher reaction rates may be achieved, but operating and capital costs increase.

The ability to isomerize hydrogenated aromatic amines and, particularly PACM, at low pressures while producing an isomer distribution approaching thermodynamic, with excellent reaction rates is achieved by the utilization of a specific catalyst system. The catalyst utilized in the isomerization process comprises cobalt, and preferably, a bimetallic mixture of cobalt in combination with a Group VIII metal or copper. In a preferred embodiment rhodium or ruthenium are coprecipitated with the cobalt catalyst. The cobalt catalyst or the bimetallic mixture of cobalt and Group VIII metal or copper components generally are carried on a support, e.g., alumina, silica, titania, or other conventional materials. Cobalt catalysts can be formed by precipitating a cobalt salt onto the support, drying and calcining. Bimetallic catalysts are formed by combining metal salts and coprecipitating onto a support.

The catalyst used for isomerization is formulated on the basis of a weight ratio of cobalt to Group VIII or copper metal of from about 0.2 to 100, preferably 3 to 60 weight parts cobalt per weight part Group VIII metal including copper metal. This catalyst system, in contrast to cobalt alone permits isomerization, after activation at 200° C., at low pressures with conversion to the thermodynamic trans, trans- isomer form being unexpectedly superior to other processes. Although the above metal weight ratio as set forth above is utilized for isomerization, a portion of the Group VIII metal, as well as copper can be incorporated into a bimetallic cobalt containing catalyst.

The cobalt and Group VIII metal containing catalyst typically is carried on a support, based upon its weight as metal, in a ratio of about 1 to 25 weight parts cobalt per 100 weight parts of support, e.g., alumina, or titania, and preferably the bimetallic catalyst comprises 1 to 20 weight parts cobalt per 100 parts support and 0.05 to 2 parts Group VIII metal or copper carried on such support.

The catalyst may be formed by coprecipitating salts of the respective metals onto a support. Coprecipitation of metal salts to produce catalyst systems is a common practice and those techniques may be used here. One advantage of a catalyst system prepared by coprecipitating cobalt with another metal salt, particularly rhodium, is that the initial reduction temperature can be reduced from a level of 400° C. and higher to about 200° C.

Catalysts having metal concentrations as stated above typically are used at catalyst levels from 0.1 to 10% by weight of the hydrogenated aromatic amine with preferred levels being from 0.5 to 5% by weight. When the amount of metal in the catalyst or the catalyst level itself approaches the lower limit of the range, the reaction rate may decrease. However, as the concentration of catalyst vis-a-vis the hydrogenated aromatic amine increases, the reaction rate generally will increase up to a point and then level off to a constant rate.

In general, the isomerization time for hydrogenated aromatic amines, e.g., PACM, can be completed within a range from about 100 to 300 minutes, at 180° C. and 100 psig, and at modest catalyst metal levels, e.g., 0.5–5% broadly and catalyst levels of 0.1–10% based on the weight of amine. Generally isomerization will not exceed 500 minutes.

Although not intending to be bound by theory, it is believed the unexpected activity of the bimetallic catalyst system, and extended catalyst life thereof, is due to the lowering of the hydrogen reduction temperature of the cobalt. To be effective, cobalt normally requires a reduction temperature of about 400° C. The isomerization reaction is carried out at much lower temperatures and, as the reaction proceeds, cobalt becomes less active. The presence of the specified Group VIII metal or copper, apparently lowers the reduction temperature of the cobalt substantially, and thus enhances its catalytic activity. On the other hand, generation of a thermodynamic isomer form of hydrogenated product is not readily explained with a bimetallic system since the isomer distribution is not representative or the average of the isomer distribution obtained with either catalyst components. For example, isomerization of PACM in the presence of cobalt, properly activated, may result in a product having a trans,trans- concentration of 50% unless it becomes deactivated; in the presence of rhodium alone the trans,trans- isomer concentration may be 15–25%; and in the presence of ruthenium alone the trans,trans- isomer concentration may be 15–25% unless high temperatures, high pressures, and long reaction times are used. Cobalt in combination with either of these metals permits one to activate the cobalt at lower temperatures and results in trans,trans- isomer distributions greater than 45% trans,trans- isomer, a value which is not representative of the average of the catalyst components.

The following examples are intended to illustrate various embodiments of the invention and all parts and percentages given are weight parts or weight percents unless otherwise specified.

EXAMPLE 1

Cobalt Catalyst Preparation a. Preparation of 4% $Co/Al_2O_3$ Catalyst

A cobalt catalyst was prepared by adding 1.98 g $Co(NO_3)_2/6H_2O$) to 7 g of deionized (DI) water. To this solution was added 10 g of activated gamma alumina. The catalyst was dried overnight at 100° C. and calcined at 400° C. for 3 hrs in air to obtain the final catalyst.

b. Preparation of 1% Ru/3% $Co/Al_2O_3$ Catalyst

A ruthenium-cobalt catalyst was prepared by dissolving a 0.21 g of $Ru_3(CO)_{12}$ in hot tetrahydrofuran (THF) and then adding 10 g of activated gamma alumina. Excess THF was evaporated with stirring. To this ruthenium catalyst was added 1.48 g of $Co(NO_3)_2/6HO_2O$ dissolved in 7 g of DI water. The mixture was stirred and then placed in a 100° C. oven overnight. The final catalyst consisting of a cobalt/ruthenium bimetallic catalyst component was obtained by calcining the catalyst at 400° C. for 3 hrs.

EXAMPLE 2

Cobalt and Ruthenium on Alumina Admixture

A catalyst system was prepared by physically admixing a commercial catalyst system of 5% $Ru/Al_2O_3$ and 4% $Co/Al_2O_3$ in a weight proportion of 5 parts of ruthenium metal to 4 weight parts of the cobalt metal.

EXAMPLE 3

Catalyst Preduction Technique

1. Catalyst Pretreatment a. Prereduction at 200° C.

Prior to catalyst use, each catalyst undergoing 200° C. reduction was charged to an empty, clean 300 cc autoclave reactor. Isopropanol (125 g) was added to the reactor and the autoclave sealed, leak tested, purged three times with nitrogen (pressurized to >200 psig, agitated, and then vented to atmospheric pressure with the agitator off). The reactor then was purged three times with hydrogen to 850 psig and vented. After venting, the reactor was pressurized to 750 psig and heated to 192° C. The system was held at temperature for two hours, cooled, vented and purged three times with nitrogen. The catalyst was recovered by filtering the mixture under a nitrogen atmosphere.

b. Prereduction at 500° C.

In a procedure similar to catalyst preduction at 200° C., each catalyst was charged to a ½" ID tubular reactor. (The autoclave was not suited for 500° C. temperatures.) Hydrogen was passed through the reactor at a rate of 20–30 cc/min. After 10 min of purging, the reactor was heated up to 500° C. The system was held at temperature for 1 hr, cooled to room temperature, and purged with nitrogen for 30 min. The catalyst was then recovered in air at room temperature.

EXAMPLE 4

Isomerization of PACM

The isomerization of PACM-20 (containing 20% of the trans,trans- isomer) was carried out by charging PACM-20 to a 300 cc autoclave batch reactor pressure vessel and contacting with under various preselected catalysts and hydrogen to determine the effectiveness of these catalysts. A 1500 rpm stirring rate was used to minimize hydrogen mass transfer as a limitation to reaction rates. After the reactants were charged, the autoclave was sealed, purged with nitrogen, followed with hydrogen and pressurized to about 600 psig with hydrogen. The autoclave was heated with agitation to the specified reaction temperature with addition of hydrogen from a ballast tank to maintain desired pressure. After the reaction was complete, the autoclave was cooled to room temperature, vented and the product mixture removed. The product was analyzed by capillary GC previously calibrated for the materials involved. Table 1 notes catalyst type, reaction conditions and yield. Table 1 sets forth the catalysts, conditions for isomerization and the results.

TABLE 1

Isomerization of 50% PACM-20[a]/THF

| Catalyst[c] | Pressure (H$_2$) | Temperature (° C.) | Time min. | % t/t | PACM (%) | Heavies[b] | Temp ° C. Reduced |
|---|---|---|---|---|---|---|---|
| 4% Co/Al$_2$O$_3$ | 750 psi | 180 | 240 | 21.0 | 100.0 | 0.0 | 200° C. reduced |
| 4% Co/Al$_2$O$_3$ | 750 psi | 180 | 240 | 53.5 | 97.6 | 2.4 | 500° C. reduced |
| 4% Co/Al$_2$O$_3$ | 100 psi | 180 | 240 | 50.2 | 98.9 | 1.1 | 500° C. reduced |
| 5% Ru/Al$_2$O$_3$ | 750 psi | 180 | 240 | 41.5 | 99.6 | 0.4 | 200° C. reduced |
| 5% Ru/Al$_2$O$_3$ | 750 psi | 180 | 240 | 41.8 | 99.5 | 0.5 | 500° C. reduced |
| 4% Ni/Al$_2$O$_3$ | 750 psi | 180 | 240 | 22.0 | 100.0 | 0.0 | 500° C. reduced |

[a]PACM-20 is PACM with 20% t/t isomer content
[b]PACM secondary amines the only byproduct produced
[c]0.78 g of catalyst was used for 110 g feed (50% PACM-20/THF)

The above results show that cobalt on alumina reduced at 200° C. or 5% Ru/Al$_2$O$_3$ or 4% Ni/Al$_2$O$_3$ was not effective for isomerizing PACM-20 to an isomer mixture having greater than 45% trans,trans- isomer content while the 500° C. cobalt catalyst was effective.

EXAMPLE 5

The isomerization procedure of Example 4 was repeated except that the ruthenium catalysts were utilized at pressures ranging from 100 to 1750 psig. The reaction conditions are set forth in Table 2.

As can be seen from Table 2, cobalt is highly effective at low pressures, e.g., 100 psig in isomerizing PACM 20 to PACM-48. Ruthenium, on the other hand, was relatively ineffective in the isomerization at 100 psig pressure.

EXAMPLE 6

Isomerization using Mixed Metal Catalysts

The procedure of Example 4 was repeated except that various mixed metal catalysts were evaluated. The results are shown in Table 3.

TABLE 2

Isomerization of 50% PACM-20[a]/THF; Effect of Pressure

| Catalyst[c] | Pressure (H$_2$) | Temperature (° C.) | Time at Temp in min. | % t/t | PACM (%) | Heavies[b] | Catalyst Reduction Conditions |
|---|---|---|---|---|---|---|---|
| 5% Ru/Al$_2$O$_3$ | 100 psi | 180 | 240 | 32.1 | 99.5 | 0.5 | 200° C. reduced |
| 5% Ru/Al$_2$O$_3$ | 750 psi | 180 | 240 | 41.5 | 99.6 | 0.4 | 200° C. reduced |
| 5% Ru/Al$_2$O$_3$ | 1700 psi | 180 | 240 | 40.2 | 99.7 | 0.3 | 200° C. reduced |
| 4% Co/Al$_2$O$_3$ | 10 psi | 180 | 240 | 21.0 | 100.0 | 0.0 | 500° C. reduced |
| 4% Co/Al$_2$O$_3$ | 100 psi | 180 | 240 | 50.2 | 98.9 | 1.1 | 500° C. reduced |
| 4% Co/Al$_2$O$_3$ | 750 psi | 180 | 240 | 53.5 | 97.6 | 2.4 | 500° C. reduced |

[a]PACM-20 has PACM with 20% t/t isomer content
[b]PACM secondary amines the only byproduct produced
[c]0.78 g of catalyst was used for 110 g of feed (50% PACM-20/THF)

TABLE 3

Isomerization of 50% PACM-20[a]/THF

| Catalyst[d] | Pressure (H$_2$) | Temperature (° C.) | Time at Temp in min. | % t/t | PACM (%) | Heavies[b] |
|---|---|---|---|---|---|---|
| 4% Co/Al$_2$O$_3$ | 750 psi | 180 | 240 | 21.0 | 100.0 | 0.0 |
| 1% Ru/3% Co/Al$_2$O$_3$ | 750 psi | 180 | 240 | 52.5 | 98.8 | 1.2 |
| 0.25% Ru/3% Co/Al$_2$O$_3$ | 750 psi | 180 | 240 | 47.8 | 99.2 | 0.8 |
| 1% Ru/Al$_2$O$_3$ | 750 psi | 180 | 240 | 24.6 | 99.9 | 0.1 |
| 1% Ru/Al$_2$O$_3$ + 4% Co/Al$_2$O$_3$[c] | 750 psi | 180 | 240 | 25.2 | 100.0 | 0.0 |
| 4% Co/Al$_2$O$_3$ | 750 psi | 180 | 240 | 21.0 | 0.0 | 0.0 |
| 1% Rh/3% Co/Al$_2$O$_3$ | 750 psi | 180 | 240 | 53.8 | 97.1 | 2.9 |
| 0.25% Rh/3% Co/Al$_2$O$_3$ | 750 psi | 180 | 240 | 54.4 | 98.1 | 1.9 |
| 0.05% Rh/3% Co/Al$_2$O$_3$ | 750 psi | 180 | 240 | 52.3 | 98.8 | 1.2 |
| 1% Rh/Al$_2$O$_3$ | 750 psi | 180 | 240 | 23.4 | 98.7 | 1.3 |
| 1% Rh/Al$_2$O$_3$ + 4% CO/Al$_2$O$_3$[c] | 750 psi | 180 | 240 | 30.0 | 99.1 | 0.9 |
| 4% Co/Al$_2$O$_3$ | 750 psi | 180 | 240 | 21.0 | 100.0 | 0.0 |
| 1% Pd/3% Co/Al$_2$O$_3$ | 750 psi | 180 | 240 | 51.3 | 97.2 | 2.8 |
| 4% Pd/Al$_2$O$_3$ | 750 psi | 180 | 240 | 22.1 | 99.4 | 0.6 |
| 4% Co/Al$_2$O$_3$ | 750 psi | 180 | 240 | 21.0 | 100.0 | 0.0 |
| 1% Pt/3% Co/Al$_2$O$_3$ | 750 psi | 180 | 240 | 54.5 | 97.3 | 2.7 |
| 4% Pt/Al$_2$O$_3$ | 750 psi | 180 | 240 | 23.5 | 98.8 | 1.2 |
| 4% Co/Al$_2$O$_3$ | 750 psi | 180 | 240 | 21.0 | 100.0 | 0.0 |
| 1% Cu/3% Co/Al$_2$O$_3$ | 750 psi | 180 | 240 | 47.8 | 99.2 | 0.8 |
| 1% Cu/Al$_2$O$_3$ | 750 psi | 180 | 240 | 22.3 | 98.9 | 1.1 |

[a]PACM-20 has PACM with 20% t/t isomer content
[b]PACM secondary amines the only byproduct produced
[c]Physical mixture of these catalyst; 0.78 g of 1% Ru/Al$_2$O$_3$ (or 1% Rh/Al$_2$O$_3$) and 0.78 g of 4% Co/Al$_2$O$_3$ per 1 feed (50% PACM-20/THF)
[d]0.78 g catalyst per 110 g feed (50% PACM-20/THF)

The above results in Table 3 show the impact of the bimetallic catalyst on the isomerization of PACM-20 to PACM-48. Isomerization can be carried out using a 200° C. prereduction of the catalyst. Physical admixtures of the catalysts, as metals, were not suited for isomerization. Isomerization could be carried out using a 500° C. reduction temperature for the cobalt catalyst when present as a physical mixture.

The results discussed in Table 2 showed that 4% Co/Al$_2$O$_3$ reduced at 200° C. (in H$_2$) was ineffective while the 4% Co/Al$_2$O$_3$ reduced at 500° C. (in H$_2$) was effective for the isomerization of PACM-20 to PACM-48. It was shown by thermogravimetric analysis (TGA) in hydrogenation that cobalt-alumina catalyst reduces itself between 300–400° C. Therefore, the difference in isomerization activity between a 200° C. reduced sample and 500° C. reduced sample is that in the former case (200° C. reduced catalyst), cobalt is not reduced while in the latter case (500° C. reduced catalyst) cobalt is reduced.

The results of Table 3 also shows that the addition of a small amount of Ru, Rh, Pd, Pt, or Cu to the cobalt-alumina catalyst makes it active for isomerization after only a reduction of 200° C. One possible reason for the synergism of this bimetallic catalysis is that the second metal (Rh, Ru, Pt, or Cu) lowers the reduction temperature of cobalt to lower than 200° C.

EXAMPLE 7

Comparative Catalyst Systems

The procedure of Example 4 was repeated except that comparative catalysts which are representative of the prior art were substituted for the catalysts employed. The reaction conditions and results are set forth in Table 4.

TABLE 4

Isomerization of 50% PACM-20[a]/THF at 180° C.

| Catalyst[c] | Pressure (H$_2$) | Temperature (° C.) | Time at Temp in min. | % t/t | PACM (%) | Heavies[b] | Catalyst Reduction Conditions/ Weight |
|---|---|---|---|---|---|---|---|
| 4% Co/Al$_2$O$_3$ | 100 psi | 180 | 240 | 50.2 | 98.8 | 1.2 | 500° C.; 0.78 g catalyst per 110 g feed[b] |
| 3% Co/1% Ru/Al$_2$O$_3$ | 100 psi | 180 | 240 | 48.8 | 99.2 | 0.8 | 200° C.; 0.78 g catalyst per 110 g feed[b] |

TABLE 4-continued

Isomerization of 50% PACM-20ª/THF at 180° C.

| Catalyst[c] | Pressure (H$_2$) | Temperature (° C.) | Time at Temp in min. | % t/t | PACM (%) | Heavies[b] | Catalyst Reduction Conditions/ Weight |
|---|---|---|---|---|---|---|---|
| Raney Cobalt | 100 psi | 180 | 240 | 32.8 | 100.0 | 0.0 | 0.78 g catalyst/ 110 g feed[b] |
| 4% Co/ Al$_2$O$_3$ | 100 psi | 180 | 240 | No isomerization | | | 200° C. reduced; this is an assumption based on 750 psi data |

[a]Same as Table 3
[b]Same as Table 3
[c]Feed is a 50% PACM-20/THF solution.

The results show that the cobalt catalysts of this invention are effective in their reduced state. Raney cobalt is sold in a reduced state and was not prereduced in accordance with prereduction procedures; cobalt on alumina was ineffective when reduced at 200° C.

What is claimed is:

1. In a process for the catalytic isomerization of hydrogenated aromatic amines from their kinetic isomer distribution to their thermodynamic isomer equilibrium ring hydrogenated counterparts, by contacting the hydrogenated aromatic amine with hydrogen in the presence of a catalyst, the improvement which comprised effecting said isomerization with a metal catalyst comprising cobalt in its reduced state, wherein said hydrogenated aromatic amine is represented by Formula I

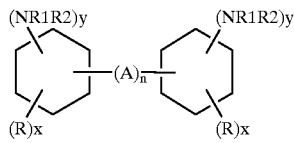

wherein R is hydrogen or C$_{1-6}$ or NH, n is 0–1, x is 1–3 and y is 0 to 2 except the sum of the y groups may be 1.

2. The process of claim 1 wherein the isomerization is conducted at a hydrogen pressure from about 50 to 4,000 psig.

3. The process of claim 2 wherein the catalyst is present in an amount from about 0.1 to 10% by weight of the hydrogenated aromatic amine.

4. The process of claim 3 wherein the catalyst is a bimetallic catalyst comprising cobalt and a Group VIII metal selected from rhodium, ruthenium, platinum, and palladium and copper and the weight ratio of cobalt to Group VIII metal or copper ranges from about 0.2 to 100 parts by weight cobalt, as metal, per weight part metal.

5. The process of claim 4 wherein R1 and R2 are hydrogen.

6. The process of claim 5 wherein A is —CH$_2$— and n is 1.

7. The process of claim 1 wherein rhodium is the metal added as a bimetallic catalyst with the cobalt to the isomerization process and the ratio of cobalt to rhodium as metal, is from about 3–60 weight parts cobalt per weight part rhodium.

8. The process of claim 1 wherein copper is the metal added as a bimetallic catalyst with the ratio of cobalt to copper as metal, is from about 3–8 weight parts cobalt per weight part copper.

9. The process of claim 1 wherein ruthenium is the metal added as a bimetallic catalyst with the ratio of cobalt to ruthenium, as metal, is from about 1 to 20 weight parts cobalt per weight part ruthenium.

10. In a process for the catalytic isomerization of bis(4-aminocyclohexyl)methane, the improvement which comprises effecting said isomerization in the presence of a catalyst comprising a bimetallic mixture of cobalt and rhodium or ruthenium carried on a support.

11. The process of claim 3 wherein the catalyst system comprises cobalt and rhodium or ruthenium and the amount of cobalt is from 4 to 8 weight parts/weight part rhodium or ruthenium, and the amount of total catalyst based on bis(4-aminocyclohexyl)methane is from 0.1 to 5% by weight.

* * * * *

UNITED STATES PATENT AND TRADEMARK OFFICE
CERTIFICATE OF CORRECTION

PATENT NO. : 6,121,493
DATED : September 19, 2000
INVENTOR(S) : Gamini Ananda Vedage and John Nelson Armor It is certified that error appears in the above-identified patent and that said Letters Patent is hereby corrected as shown below:

<u>Column 11, line 30 through Column 12, line 55,</u>
Replace claims 1, 3-9, and 11 with the following claims:

1. In a process for the catalytic isomerization of hydrogenated aromatic amines from their kinetic isomer distribution to their thermodynamic isomer equilibrium ring hydrogenated counterparts, by contacting the hydrogenated aromatic amine with hydrogen in the presence of a catalyst, the improvement which comprised effecting said isomerization with a metal catalyst comprising a bimetallic mixture of cobalt with a Group VIII metal or copper wherein said hydrogenated aromatic amine is represented by Formula I

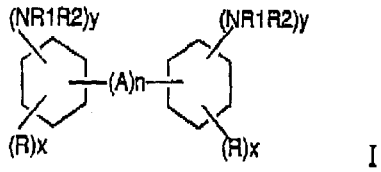

wherein R is hydrogen or $C_{1-6}$ or NH, n is 0-1, x is 1-3 and y is 0 to 2 except the sum of the y groups may be 1.

3. The process of Claim 2 wherein the catalyst is present in an amount from about 0.1 to 10% by weight of the hydrogenated aromatic amine and the hydrogen pressure is from about 100 to 1000 psig.

4. The process of Claim 3 wherein the Group VIII metal selected from the group consisting of rhodium, ruthenium, platinum, and palladium and the weight ratio of cobalt to Group VIII metal or copper ranges from about 0.2 to 100 parts by weight cobalt per weight part Group VIII metal or copper, and the amount of catalyst is 0.5 to % by weight of the hydrogenated aromatic amine.

5. The process of Claim 4 wherein R, R1 and R2 are hydrogen, x = 1, and y = 1.

6. The process of Claim 5 wherein A is -$CH_2$- and n is 1.

7. The process of Claim 6 wherein rhodium is the metal added as a bimetallic catalyst with the cobalt to the isomerization process and the ratio of cobalt to rhodium as metal, is from about 3-60 weight parts cobalt per weight part rhodium.

8. The process of Claim 6 wherein copper is the metal added as a bimetallic catalyst with the ratio of cobalt to copper as metal, is from about 3-8 weight parts cobalt per weight part copper.

9. The process of Claim 6 wherein ruthenium is the metal added as a bimetallic catalyst with the ratio of cobalt to ruthenium is from about 1 to 20 weight parts cobalt per weight part ruthenium

UNITED STATES PATENT AND TRADEMARK OFFICE
CERTIFICATE OF CORRECTION

PATENT NO.    : 6,121,493
DATED         : September 19, 2000
INVENTOR(S)   : Gamini Ananda Vedage and John Nelson Armor It is certified that error appears in the above-identified patent and that said Letters Patent is hereby corrected as shown below:

Columns 11 and 12 (cont'd),

11. The process of Claim 10 wherein the amount of cobalt is from 4 to 8 weight parts/weight part rhodium or ruthenium, and the amount of total catalyst based on bis(4-aminocyclohexyl)methane is from 0.1 to 5% by weight.

Signed and Sealed this

Thirteenth Day of April, 2004

JON W. DUDAS
*Acting Director of the United States Patent and Trademark Office*